(12) United States Patent
Eistert

(10) Patent No.: US 6,814,077 B1
(45) Date of Patent: Nov. 9, 2004

(54) TRACHEAL CANNULA

(75) Inventor: Bernhard Eistert, Rothenburg ob der Tauber (DE)

(73) Assignee: Maria Zylka-Eistert, Rothenburg ob der Tauber (DE)

( * ) Notice: Subject to any disclaimer, the term of this patent is extended or adjusted under 35 U.S.C. 154(b) by 0 days.

(21) Appl. No.: 10/019,714

(22) PCT Filed: Aug. 6, 1999

(86) PCT No.: PCT/EP99/05696
§ 371 (c)(1),
(2), (4) Date: Dec. 28, 2001

(87) PCT Pub. No.: WO01/10490
PCT Pub. Date: Feb. 15, 2001

(51) Int. Cl.[7] ............................................. A62B 9/06
(52) U.S. Cl. ........................ 128/207.14; 128/207.15; 128/207.16
(58) Field of Search .................. 128/207.14, 207.15, 128/207.16

(56) References Cited

U.S. PATENT DOCUMENTS

| | | | |
|---|---|---|---|
| 3,924,637 A | | 12/1975 | Swanson |
| 4,037,605 A | * | 7/1977 | Firth .................... 128/207.14 |
| 4,459,984 A | * | 7/1984 | Liegner ................ 128/207.15 |
| 4,538,607 A | * | 9/1985 | Saul ..................... 128/207.16 |
| 4,573,460 A | * | 3/1986 | Szachowicz et al. ... 128/200.26 |
| 4,627,433 A | * | 12/1986 | Lieberman ............ 128/207.16 |
| 4,751,924 A | * | 6/1988 | Hammerschmidt et al. ..................... 128/207.15 |
| 4,759,356 A | * | 7/1988 | Muir .................... 128/207.16 |
| 4,794,924 A | * | 1/1989 | Eliachar ............... 128/207.16 |
| 4,852,565 A | * | 8/1989 | Eisele .................. 128/207.14 |
| 4,921,642 A | * | 5/1990 | Latorraca ............. 261/142 |
| 5,056,515 A | * | 10/1991 | Abel .................... 128/207.15 |
| 5,177,996 A | * | 1/1993 | Sahakian .............. 73/40 |
| 5,392,775 A | * | 2/1995 | Adkins, Jr. et al. .... 128/207.16 |
| 5,419,314 A | * | 5/1995 | Christopher .......... 128/200.26 |
| 5,765,558 A | * | 6/1998 | Psaros et al. ......... 128/207.14 |
| 5,771,888 A | | 6/1998 | Keim |
| 5,957,978 A | * | 9/1999 | Blom ................... 623/9 |
| 5,964,221 A | * | 10/1999 | McKenna ............. 128/205.12 |
| 6,039,696 A | * | 3/2000 | Bell ..................... 600/532 |
| 6,135,111 A | * | 10/2000 | Mongeon ............. 128/207.15 |
| 6,503,303 B2 | * | 1/2003 | Fuesser ................ 96/380 |

FOREIGN PATENT DOCUMENTS

| | | |
|---|---|---|
| DE | 296 13 819.3 | 8/1996 |
| EP | 83630144.0 | 9/1983 |

OTHER PUBLICATIONS

TESS trademark record for Teflon Reg. # 1111147, filed Jun. 15, 1978.*
TESS trademark record for Goretex Reg # 2079739, filed Mar. 21, 1995.*
Stedman's Medical Dictonary 26th Ed. p. 1830, Definition of tracheotomy.*
Alexander's Care of the Patient in Surgery 10th ed, Anatomy of the larynx & trachea.*

* cited by examiner

Primary Examiner—Amanda R. Flynn
(74) Attorney, Agent, or Firm—Alix, Yale & Ristas, LLP

(57) ABSTRACT

A tracheal cannula (1) which is inserted into the trachea (9) after tracheotomy. The cannula comprises a shaft (2) and a cuff (3) to block the tracheotomy surrounding the shaft (2). Speaking is made possible even in the case of patients at risk for aspiration due to the fact that a membrane-protected window (4) is embodied in the section of the shaft (2) located above the cuff (3).

20 Claims, 2 Drawing Sheets

TRACHEAL CANNULA

BACKGROUND OF THE INVENTION

This invention relates to a tracheal cannula for insertion into the trachea following a tracheotomy, with this cannula having a shaft and a cuff for blocking the tracheal cross-sectional area surrounding the shaft.

Following a tracheotomy, a cannula is inserted into the trachea in order to keep open the lumen thereby created. Available to this end are cannulas in diverse forms and made of various materials. Thus, thin-walled silver cannulas are familiar that are constructed in a double-barreled form, namely, they have an outer cannula and an inner cannula that is easy to remove. Furthermore, there are also more thick-walled plastic cannulas that, in contrast to metal cannulas, are not as rigid and that at body temperature conform roughly to the shape of the surrounding space, without their lumen thereby changing.

When there is an increased risk of aspiration, a tracheal cannula with a so-called blocker cuff is used, which is intended to prevent any entering of saliva, gastric juice, or other fluids or food (aspiration). These cuffs are normally positioned around the shaft of the cannula or are integrated within it, and can be inflated in order to conform to the surrounding space of the trachea.

Finally there are artificial larynxes, which are equipped with a valve mechanism and a hole or a screen on their shaft in order to make it possible for the patient to vocalize. When the patient inhales, the valve mechanism at the cannula entrance opens up and permits the intake of air through the cannula into the lungs. On the other hand, in exhalation the valve closes and the air stream is led out through the larynx in a normal way via the cannula hole or window, thus enabling both a normal air intake and also the use of the voice. However, such artificial larynxes can be used only in patients who are not at risk for aspiration, so that those who are at such a risk have no way to speak. Whereas this is still tolerable for patients in the transitional stage immediately after a tracheotomy, the inability to vocalize over a long period of time is quite difficult to accept, especially in the case of neurologically impaired patients with a protracted risk for aspiration (for example, following a stroke).

Known from U.S. Pat. No. 4,459,984 is a tracheal cannula of this species for insertion into the trachea. This device comprises a curved cannula that has an inflatable cuff positioned around the end of the cannula that is within the trachea. Above the cuff, the tracheal cannula has an escape nozzle or opening that can be closed by a flap valve and that can be opened by increasing the air pressure in the tracheal cannula, so that air escapes into the upper esophagus and the patient can speak during the mechanical evacuation of air. However, because of this valve, which is intended to prevent aspiration when in the closed state, the air stream is deflected and slowed down considerably. This causes the natural vocalization characteristics in the larynx to be impaired. Furthermore, when the inner pressure in the tracheal cannula slackens, the valve is abruptly closed and thereby prevents vocalization from continuing. Moreover, due to the possibility that the flap of the valve may jam, a risk of aspiration cannot be excluded with certainty.

Therefore, one object of the invention is to make possible in a reliable way a vocalization that is as natural as possible in patients equipped with tracheal cannulas that have a cuff.

SUMMARY OF THE INVENTION

By means of the invention, this object is essentially achieved by constructing a window in the section of the shaft lying above the cuff, with this window being covered by a membrane that is permeable to air. This membrane thereby prevents the entry of saliva and food particles into the cannula and thus into the lower airways. But on the other hand, speaking is made possible because of the air permeability of the membrane.

In accordance with one preferred embodiment of the invention, the membrane is not permeable to water, so as to ensure that no saliva or nutrient components enter into the cannula. It has turned out to be especially advantageous in this connection to use a membrane made of polytetrafluoroethylene (PTFE), especially a fabric made of PTFE such as can be obtained on the commercial market under the trade name of Gore-Tex®.

In the inhalation process the air is carried through the cannula into the lungs, whereas for speaking purposes the patient can hold closed the cannula in order for the air to go through the membrane into the larynx. However, in accordance with one preferred embodiment of the invention, a provision is made to have a valve situated at the entrance of the cannula, with this valve automatically opening with inhalation and closing with exhalation.

In one improvement of the invention, the cuff is connected via a line to a pilot balloon or the like for the inflation of the cuff and for controlling the cuff pressure.

Other aims, advantages, and possible applications of the invention appear from the following description of an exemplary embodiment and from the drawings. Here all the described and/or graphically represented features form the subject of the invention by themselves or in any given combination, regardless of how they are summarized in the claims or of any of their back-references.

DETAILED DESCRIPTION OF THE PREFERRED EMBODIMENT

Figure 1:
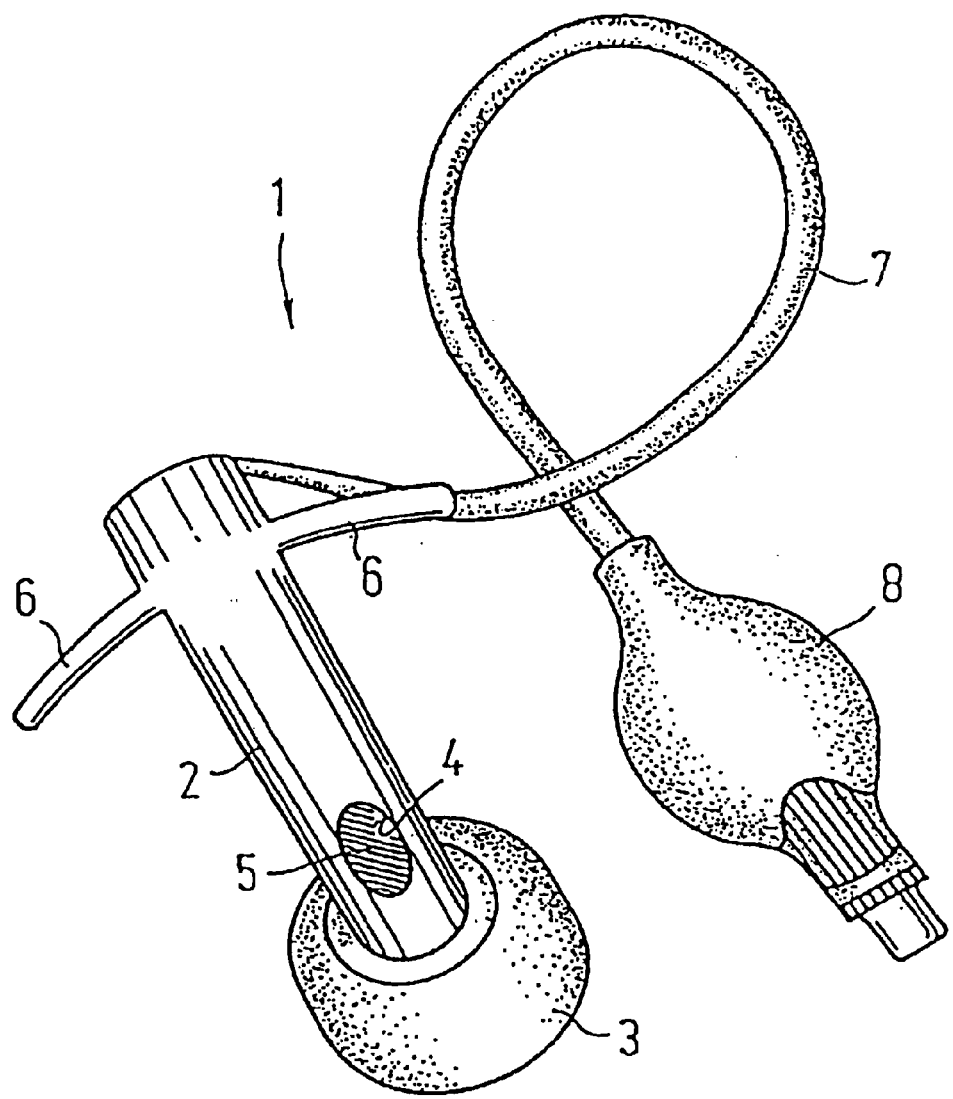
FIG. 1 is a schematic view of a tracheal cannula in accordance with the invention.

As can be seen from the drawings, a tracheal cannula 1 in accordance with the invention comprises a hollow shaft 2, within whose lower section a cuff 3 is provided. This cuff 3 can be slipped onto the shaft 2 or can be constructed to form a one-piece unit with this. Above the cuff 3 a window 4 is constructed in the shaft 2, with this window being covered with an air-permeable but not water-permeable membrane 5. In one preferred embodiment, the membrane consists essentially of polytetrafluoroethylene (PFTE) or a fabric made of PFTE lacing This membrane preferably is composed of a fabric such as can be obtained on the commercial market under the trade name of Gore-Tex®.

Provided at the front section of the shaft 2 are holding arms 6 by means of which the positioning and attachment of the tracheal cannula 1 on the throat of the patient can be accomplished. Via a line 7, which is connected with a pilot balloon 8, the cuff 3 can be inflated and the cuff pressure can be controlled. The line 7 can be designed to be removable from the cannula.

Figure 2:
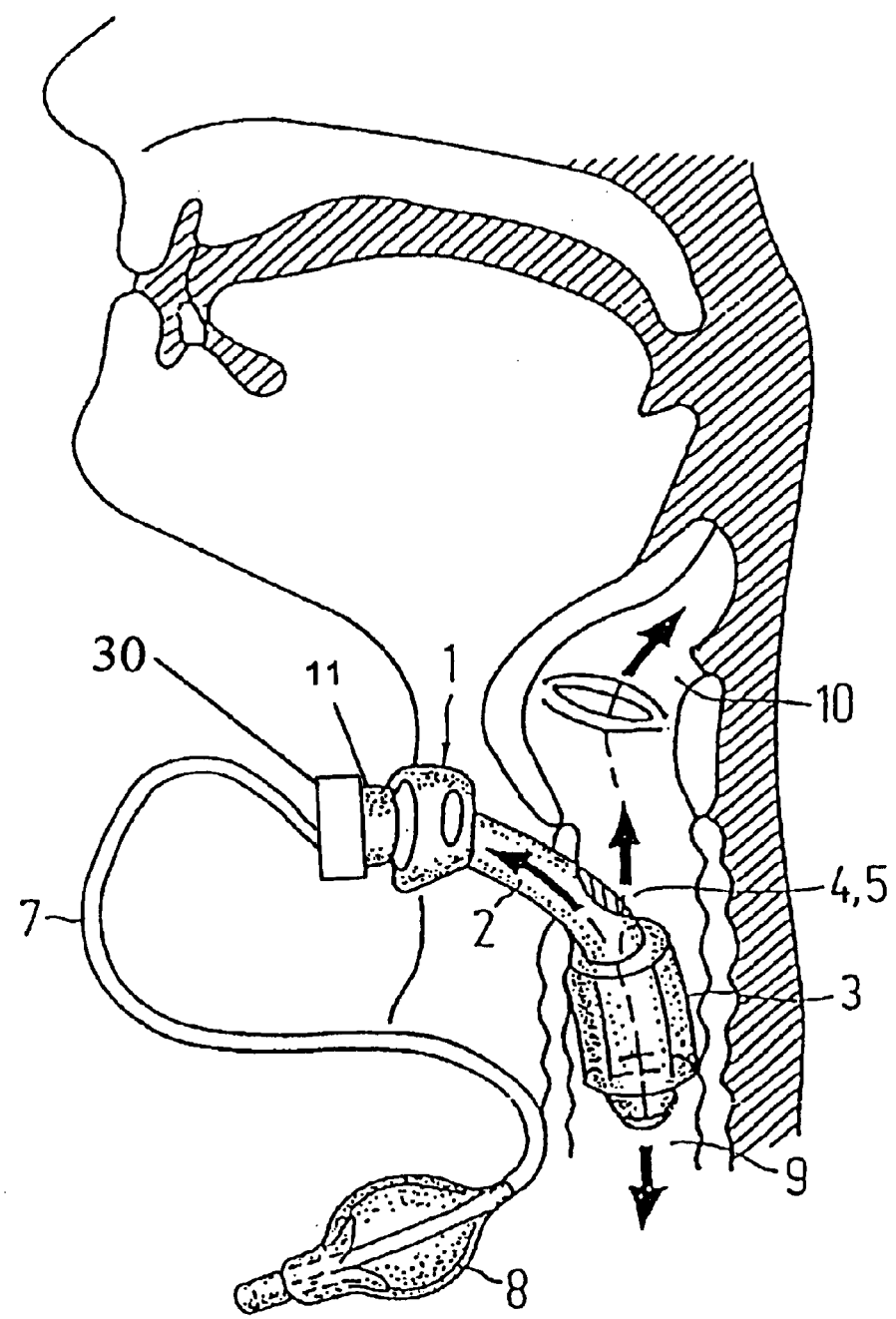
FIG. 2 is the tracheal cannula shown in schematic fashion when inserted into the trachea of a patient.

Following a tracheotomy the tracheal cannula 1 is shown as in FIG. 2, with it being inserted into the trachea 9 of the patient. In this connection, it must be made sure that the membrane-protected window 4 of the shaft 2 lies within the tracheal lumen of the trachea 9, so that in an exhalation it is ensured that the air is carried into the larynx 10. After the insertion of the tracheal cannula 1, the cuff 3 is inflated with the aid of the pilot balloon 8 or in some other suitable way such that it conforms to the cross-sectional area of the trachea and thus closes the trachea. Thereby the lungs can be supplied with air only via the cannula 1.

In inhalation, the air is sucked in through the intake 11 of the tracheal cannula 1 and is conveyed into the lungs. When exhaling, a valve 30 closes the cannula 1, so that the air stream escapes through the membrane-protected window 4 into the larynx 10 and the patient is rendered able to speak.

In a different, simpler embodiment, no valve is provided in the tracheal cannula 1, so that in order to speak the patient must hold shut the cannula 1 during the exhalation process.

In this way, by means of the invention any entry of fluid into the trachea is reliably prevented, whereas in exhaling the air goes through the membrane into the larynx, so that the patient is able to speak.

What is claimed is:

1. A tracheal cannula for insertion through a tracheotomy incision into a patient's trachea, at a position below the larynx, the trachea having a cross-sectional area, said cannula having a shaft and a cuff for blocking the tracheal cross-sectional area surrounding the shaft wherein a shaft section extends above the cuff, characterized in that section of the shaft lying above the cuff has a window covered by an air-permeable membrane, wherein the air-permeable membrane has sufficient permeability to allow for patient vocalization.

2. The cannula based on claim 1, characterized such that the membrane is not permeable to water.

3. The cannula based on claim 2, characterized such that the membrane consists essentially of polytetrafluoroethylene (PTFE).

4. The cannula based on claim 2, characterized such that the membrane comprises polytetrafluoroethylene (PTFE).

5. The cannula based on claim 3, characterized such that the membrane comprises a fabric made of PTFE lacing.

6. The cannula based on claim 4, characterized in that the membrane consists of a fabric made of PTFE lacing.

7. The cannula based on claim 1, characterized such that at the entrance of the cannula, a valve is provided which opens upon inhalation and closes upon exhalation.

8. The cannula based on claim 2, characterized such that at the entrance of the cannula, a valve is provided which opens upon inhalation and closes upon exhalation.

9. The cannula based on claim 3, characterized such that at the entrance of the cannula, a valve is provided which opens upon inhalation and closes upon exhalation.

10. The cannula based on claim 4, characterized such that at the entrance of the cannula, a valve is provided which opens upon inhalation and closes upon exhalation.

11. The cannula based on claim 5, characterized such that at the entrance of the cannula, a valve is provided which opens upon inhalation and closes upon exhalation.

12. The cannula based on claim 6, characterized such that at the entrance of the cannula, a valve is provided which opens upon inhalation and closes upon exhalation.

13. The cannula based on claim 1, characterized such that the cuff is connected via a line to balloon means for the inflation of the cuff and for controlling the cuff pressure.

14. The cannula based on claim 2, characterized such that the cuff is connected via a line to balloon means for the inflation of the cuff and for controlling the cuff pressure.

15. The cannula based on claim 3, characterized such that the cuff is connected via a line to balloon means for the inflation of the cuff and for controlling the cuff pressure.

16. The cannula based on claim 4, characterized such that the cuff is connected via a line to balloon means for the inflation of the cuff and for controlling the cuff pressure.

17. The cannula based on claim 5, characterized such that the cuff is connected via a line to balloon means for the inflation of the cuff and for controlling the cuff pressure.

18. The cannula based on claim 6, characterized such that the cuff is connected via a line to balloon means for the inflation of the cuff and for controlling the cuff pressure.

19. The cannula based on claim 7, characterized such that the cuff is connected via a line to balloon means for the inflation of the cuff and for controlling the cuff pressure.

20. The cannula based on claim 13, wherein said balloon means comprises a pilot balloon.

* * * * *